United States Patent [19]

Monsigny

[11] Patent Number: 4,576,745

[45] Date of Patent: Mar. 18, 1986

[54] METHOD FOR THE FLUORIMETRIC DETERMINATION OF ENDOTOXINS, NEW PEPTIDES CARRYING A FLUOROPHOROUS SUBSTANCE USABLE IN SAID METHOD AND METHOD FOR ITS PREPARATION

[75] Inventor: Michel Monsigny, Saint-Cyr-en-Val, France

[73] Assignee: Centre National de la Recherche Scientifique, Paris, France

[21] Appl. No.: 422,976

[22] PCT Filed: Jan. 6, 1982

[86] PCT No.: PCT/FR82/00003

§ 371 Date: Sep. 9, 1982

§ 102(e) Date: Sep. 9, 1982

[87] PCT Pub. No.: WO82/02382

PCT Pub. Date: Jul. 22, 1982

[30] Foreign Application Priority Data

Jan. 9, 1981 [FR] France ............................... 81 00261

[51] Int. Cl.$^4$ ........................................... C07C 103/52
[52] U.S. Cl. .............................................. 260/112.5 R
[58] Field of Search ................................. 260/112.5 R

[56] References Cited

PUBLICATIONS

The Embo Journal, vol. 1 (1982) 303–306.
FEBS Letters 157, No. 2 (1983) 265–270.

*Primary Examiner*—Delbert R. Phillips
*Attorney, Agent, or Firm*—Beveridge, DeGrandi & Weilacher

[57] ABSTRACT

Method for determining endotoxins in a liquid, wherein said liquid is contacted, at 20°–40° C., with a lysate of limule amebocytes and an aqueous solution of a peptide having the following formula:

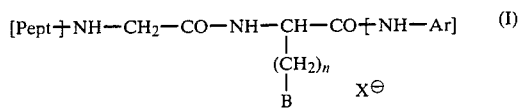

in which [Pept⫤ is a peptidic hydrophobic chain, n is 1, 2, 3, 4, or 5, B is

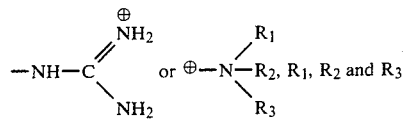

being H or CH$_3$, ⫤NH—Ar] is the residue of a fluorescent heteroaromatic amine and X$^\ominus$ is an anion, the pH of the thus obtained medium is adjusted at 5 to 10 and the heteroaromatic amine thus formed is determined by fluorimetry, and new peptides according to formula (I) usable in said method.

4 Claims, No Drawings

METHOD FOR THE FLUORIMETRIC DETERMINATION OF ENDOTOXINS, NEW PEPTIDES CARRYING A FLUOROPHOROUS SUBSTANCE USABLE IN SAID METHOD AND METHOD FOR ITS PREPARATION

The subject of the present invention is a method for the fluorimetric determination of endotoxins (bacterial lipopolysaccharides or lipopolyosides) using a peptide carrying a fluorophorous substance. The invention also relates to new peptides carrying a fluorophorous substance usable in the said method and their method of preparation.

It is known that endotoxins can be determined by measuring the rise in temperature caused in rabbits (cf. for example French Pharmacopoeia, 9th edition, II-235 to II-238), by measuring the time of formation of a gel from a Limule amebocytes lysate (cf. for example Cooper, Levin, Wagner, J. Lab. Cli. Med., July 1971, 138–148) and by colorimetry with the aid of p-nitroaniline (cf. Iwanaga et al., Haemostasis 7, 183–188, 1978; Harada et al., Progress in Clinical and Biological Research, vol. 29, 1979, 209–220). These methods are generally not quantitative and in addition their sensitivity is not sufficient to enable very small quantities of endotoxins to be detected (quantities in the neighborhood of a picogram).

It has also been suggested (cf. U.S. Pat. No. 4,188,264) that endotoxins could be determined by a fluorimetric method using a peptide substrate of the formula:

$$R-Gly-Arg-R' \quad (A)$$

in which R is a residue of an L amino acid or peptide, whose terminal amino group is protected by a protective group, and R' is the residue of beta-naphthylamine or a fluorescent hydroxylated compound selected from alpha and beta naphthol, indoxyl, N-methyl indoxyl, 4-methyl umbelliferone and resorufin. The peptide substrates of formula (A) for which R' represents the residue of a fluorescent hydroxylated compound have the disadvantage of hydrolyzing spontaneously in aqueous solution.

A method for determining endotoxins by fluorimetry in liquids has now been found in accordance with the present invention which enables endotoxins to be determined quantitatively with a very high sensitivity. This method does not have the disadvantage pointed out above for the fluorimetric method using peptide substrates of formula (A) for which R' is the residue of a fluorescent hydroxylated compound. In addition, it has a markedly greater sensitivity than the fluorimetric method using peptide substrates of formula (A) for which R' is the residue of beta-baphthylamine.

The method according to the invention consists in bringing the liquid to be analyzed into contact, at a temperature between 20° C. to 40° C., with a limule amebocytes lysate and an aqeuous solution of a peptide of the formula:

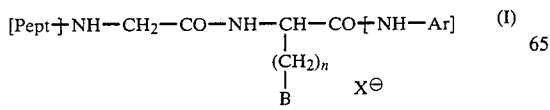

in which [Pept⫫ designates a hydrophobic peptide chain, n is equal to 1, 2, 3, 4 or 5, B is a radical:

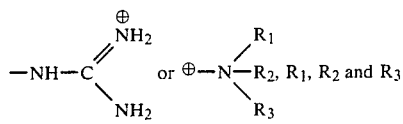

designating hydrogen atoms or methyl groups; ⫫N-H—Ar] designates the remainder of a fluorescent heteroaromatic amine Ar—NH₂ containing one or several heteroatoms selected from the oxygen, sulfur and nitrogen atoms, whose fluorescence spectrum is markedly displaced by acylation of the amine, and X⊖ designates an anion, in particular the Cl⊖ anion, in adjusting if necessary the pH of the medium thereby obtained to a value between 5 and 10, the determining by fluorimetry the heteroaromatic amine Ar—NH₂ formed.

In the method according to the invention, the contact is established preferably at a temperature in the range of 25° C. to 37° C. and the pH of the medium is preferably adjusted to a value in the range of 6–7.5.

By a fluorescent heteroaromatic amine Ar—NH₂ whose fluorescence spectrum is markedly displaced by acylation of the amine is intended, within the scope of the present invention, any primary heteroaromatic amine whose fluorescence intensity at the emission wavelength of said free amine is at least 100 times greater than the fluorescence intensity, at this same wavelength, of the corresponding compounds of formula (I). For this condition to be met, it is generally necessary for the wavelength corresponding to the maximum emission of the free amine to be shifted by at least 50 nm towards the longest wavelength with respect to the wavelength corresponding to the maximum emission of the corresponding compounds of formula (I). As fluorescent heteroaromatic amines Ar—NH₂ meeting the above conditions can be cited for example 7-amino 4-methyl coumarin, 7-amino 4-trifluoromethyl coumarin, 7-amino 4-nitro 2-oxa 1,3-benzodiazole and more particularly 3-amino 9-ethyl carbazole.

In the formula (I) above, "n" is preferably equal to 3 and B is preferably a

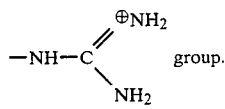

group.

The number of amino acid links of the peptide chain [Pept⫫ of the peptides of formula (I) is not limited. This number however, is preferably equal to 1 or 2. As examples of the hydrophobic peptide chain [Pept⫫ can be cited the following chains:

[Val—Leu⫫,

[Ser(OBz)⫫,

[Ile—Glu(γ—OCH₃)⫫,

[Val⫫,

[Leu⫫,

[Val—Ser⫫, chains in which Val designates the valine link, Leu the leucine link, Ile the isoleucine link, Ser the serine link, Ser (OBz) the serine link in which the CH₂OH group is replaced by the group CH₂—O—CH₂—C₆H₅ and Glu (γ—OCH₃) the glutamic acid link in which the COOH group in the gamma position is replaced by the COOCH₃ group.

In the examples of hydrophobic peptide chains [Pept—] above, the amino group NH₂ of the amino acid link, when there is only one link, and the NH₂ amino group of the amino acid link on the left, when there are two links, can be nonsubstituted or substituted by a tertiobutyloxycarbonyl (t Boc), benzyloxycarbonyl, benzyl, tosyl or acyl, in particular acetyl or benzoyl, group.

The method of determining endotoxins according to the invention is based on the property which endotoxins have of activating a protease contained in the limule amebocytes lysate (Limulus polyphemus). In the absence of endotoxin, the protease does not act on the peptides of formula (I). In the presence of endotoxin, the protease hydrolyzes the peptides of formula (I) with liberation on one hand of peptides of the formula:

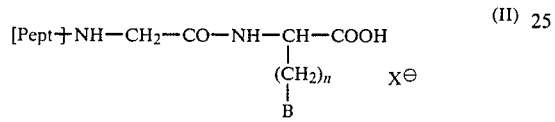  (II)

in which [Pept—], n, B and X⊖ have the same meanings as in formula (I) and on the other hand of the fluorescent heteroaromatic amine Ar—NH₂. The activity of the protease is strictly proportional to the concentration of endotoxin in the medium. Consequently the concentration in the medium of the liberated amine Ar—NH₂ and the fluorescence intensity measured at the emission wavelength of said free amine are, at a given moment after contacting the liquid containing the endotoxin, the limule amebocytes lysate and the peptide of formula (I), strictly proportional to the concentration of endotoxin in the medium.

According to a first embodiment of the method according to the invention, the liquid to be analyzed, the limule amebocytes lysate and the aqueous solution of the peptide of formula (I) are allowed to remain in contact, after any necessary adjustment of the pH and at the previously indicated temperature, during a defined time fixed beforehand which is preferably 10 minutes to 30 minutes, after which is added to the medium a compound which stops the hydrolysis of a peptide of formula (I) without interfering adversely with the fluorescence of the heteroaromatic amine Ar—NH₂ formed, and the heteroaromatic amine Ar—NH₂ formed is determined by measuring the fluorescence intensity at the emission wavelength of the free amine. As compound stopping the hydrolysis of the peptide of formula (I) without interfering adversely with the fluorescence of the heteroaromatic amine Ar—NH₂ can be cited benzamidine, ortho-amino benzamidine and para-amino benzamidine.

According to a second embodiment of the method according to the invention, the fluorescence intensity at the emission wavelength of the free amine is recorded continuously as soon as the liquid to be analyzed, the limule amebocytes lysate and the aqueous solution of the peptide of formula (I) have been brought into contact and the pH adjusted if necessary, the temperature being maintained constant at a value situated in the previously defined range. This second operating procedure, called kinetic method, enables the hydrolysis time to be adjusted without any trial and error process to the quantity of endotoxins present in the sample to be analyzed.

The method according to the invention enables endotoxins to be determined in various liquids (injectable aqueous solutions of natural or synthetic products, solutions of proteins, physiological liquids such as serum, plasma, urine, etc.). It is particularly sensitive since it enables quantities of endotoxin in the neighborhood of one hundredth of a picogram to be detected. In addition it enables endotoxins to be determined quantitatively with a precision of the order of a few percent; it is rapid and can be made automatic. By way of comparison, the method based on the measurement of the time of formation of a gel does not allow quantities of endotoxins less than 30 picograms to be detected, is relatively long (duration: 1 hour), and is only semi-quantitative.

The peptides of formula (I) for which n is equal to 3, B is the residue

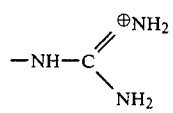

and —NH—Ar] is the residue of 7-amino 4-methyl coumarin or 7-amino 4-trifluoromethyl coumarin are known products which have been recommended for the fluorimetric determination of certain enzymes (cf. European patent applications Nos. 0 000 063 and 0 018 112 and the international patent application No. WO 79/00602).

The peptides of formula (I) for which —[NH—Ar] is the residue of 7-amino 4-nitro 2-oxa, 1,3-benzodiazole or 3-amino-9-ethyl carbazole are new products and as such are part of the invention.

In general, the peptides of the general formula (I), and in particular those which are new, can be prepared by reacting, in the presence of an activating compound of the COOH group and 1-hydroxy benzotriazole, the fluorescent heteroaromatic amine Ar—NH₂ with the peptides of the general formula:

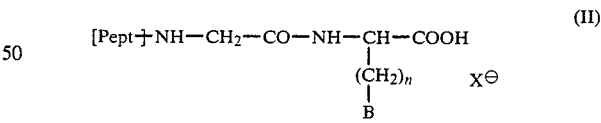  (II)

in which [Pept—], n, B and X⊖ have the same meanings as in formula (I). As activating compounds of the COOH group that may be used can be cited those mentioned by Konig W., Geiger R., Chem. Ber. 103, (1970), 788–798 and by Gross E., Meienhofer J. (The peptides: Analysis, synthesis and biology. I. Major Methods of peptide bond formation, Academic Press, 1979, p. 435), and in particular dicyclohexylcarbodiimide.

The peptides of general formula (II) are known products which can be obtained by conventional peptide synthesis methods (cf. Konig, W., Geiger R. and Gross E., Meienhofer J., already cited).

The following examples illustrate the invention without limiting it.

EXAMPLE 1

Preparation of peptides of formula (I)

One millimole of peptide of the formula:

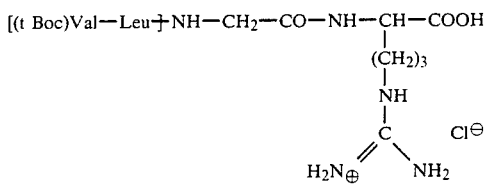
(III)

in which Leu designates the leucine link and (t Boc) Val the valine link in which the amino group NH2 is substituted by a tertiobutyloxycarbonyl group, and a millimole of p-toluenesulfonic acid are dissolved in 2 ml of redistilled dimethylformamide free from amines. To this solution, cooled to 0° C. and maintained under a nitrogen atmosphere, are added one millimole of 3-amino 9-ethyl carbazole, 1 millimole of 1-hydroxybenzotriazole and 1 millimole of dicyclohexylcarbodiimide. The reaction mixture is maintained at 0° C. for 2 hours, and then at 25° C. for 18 hours. The dicyclohexylurea formed is precipitated by maintaining the mixture at 0° C. for 24 hours, and then separated by filtration or centrifugation. The dimethylformamide is removed by evaporation under reduced pressure. The residue obtained which contains, in the raw state, the peptide carrying the fluorophorous substance, is dissolved in a mixture containing 80 parts by volume of chloroform, 20 parts by volume of methanol and 3 parts by volume of water and then fixed on a silica gel column and eluted with the above mixture. The fractions containing the peptide carrying the fluorophorous substance are evaporated under reduced pressure.

The peptide of the following formula is thus obtained in a pure state:

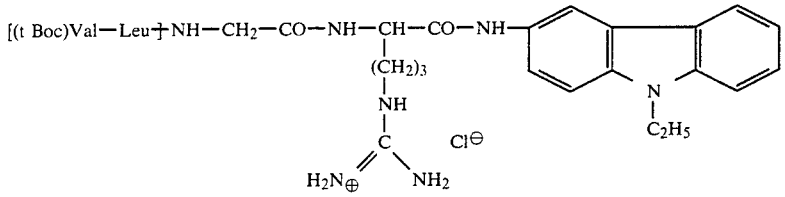
(IV)

The purity and identity of the product obtained are proved, interalia, by thin layer chromatographic analysis and absorption and fluorescence spectra. Contrary to 3-amino 9-ethyl carbazole which, when excited at 362 nm, exhibits very strong fluorescence (200 units of fluorescence) at 460 nm, the peptide of formula (IV), when excited at 362 nm, exhibits only very weak fluorescence (one unit of fluorescence) at 460 nm.

EXAMPLES 2 to 4

Preparation of peptides of formula (I)

By proceeding as in example 1, but replacing 3-amino 9-ethyl carbazole by 7-amino 4-methyl coumarin, 7-amino 4-trifluoromethyl coumarin or 7-amino 4-nitro 2-oxa 1,3-benzodiazole, the following peptides of formulas (V), (VI) and (VII) are obtained:

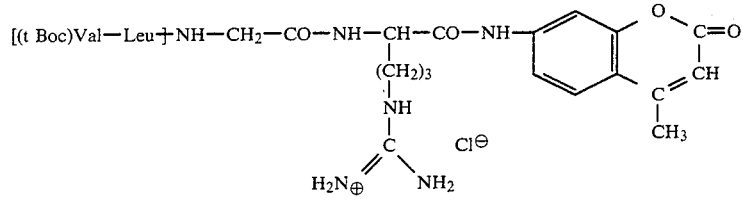
(V)

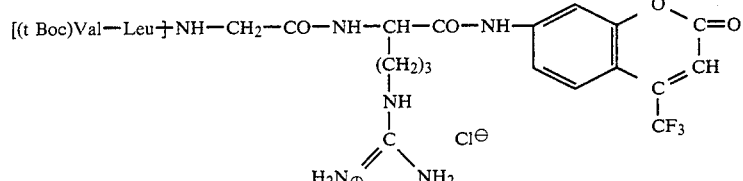
(VI)

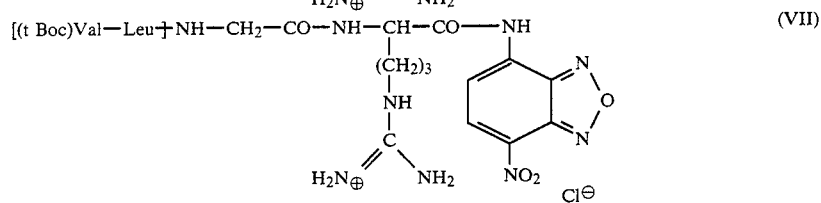
(VII)

EXAMPLE 5

Application of peptides of formula (I) in the determination of endotoxins

A quantity of peptide of formula (IV) is dissolved in water so that the solution obtained gives, in the 1 cm thick cell and at a wavelength of 340 nm, an absorption equal to 0.1. To 400 μl of this solution are added 200 μl of limule amebocytes lysate (lysate for Limulus test marketed by Mallenkroot) and 200 µl of liquid to be analyzed containing endotoxins, the pH of the liquid having if necessary previously been adjusted to a value between 6 and 7.5. The mixture obtained thereby is then treated in accordance with either of the following operating procedures (a) or (b):

(a) The mixture is maintained at 25° C. (or 37° C.) for 30 minutes, and 0.2 ml of a 25 mM solution of benzamidine in dimethylformamide are then added to stop the hydrolysis reaction and, within the following hour, the fluorescence intensity is read at a wavelength of 460 nm, the excitation wavelength being 362 nm and the solution being maintained at a constant temperature (for example 25° C.) at the time of the reading.

(b) The mixture is maintained at 37° C. and the fluorescence intensity recorded continuously at a wavelength of 460 nm, the excitation wavelength being 362 nm.

In both cases, the fluorescence intensity obtained is compared with that given, under the same conditions, by a reaction mixture containing 400 µl of the solution of peptide of formula (IV), 200 µl of the limule amebocytes lysate and 200 µl of a 50 pg/ml standard solution of endotoxin. The content of endotoxin of the liquid under analysis is obtained by comparison of the results.

It is possible to eliminate any interference with the determination of the endotoxins of the proteases contained in the liquid under analysis, in particular in the case where this liquid is a physiological liquid, by performing the following test:

The liquid under analysis, whose pH is adjusted if necessary to 7.0, is heated for 10 minutes at 100° C. Any precipitate formed is removed by centrifugation and the supernatant part is used for the determination of endotoxins according to the previously described prodecure. If the result obtained is the same as that obtained using the physiological liquid not treated at 100° C., the result obtained with the untreated liquid is correct. If the result obtained with the liquid treated at 100° C. is less than that obtained wih the untreated liquid, only the result obtained with the liquid treated at 100° C. will be adopted.

It is also possible to check the absence of proteases in the liquid to be analyzed or on the contrary the absence of products inhibiting the hydrolysis of the peptide of formula (IV) and to take account, in the contrary case, during the determination of endotoxins, of the presence of these proteases or products in the sample to be analyzed by proceeding as follows:

Solutions A, B, C, D of composition given in the following table are prepared.

|  | A | B | C | D |
|---|---|---|---|---|
| Limule amebocytes lysate | 0 | 200 µl | 200 µl | 200 µl |
| Phosphate buffer solution 0.025 M - pH 7.4 | 300 µl | 100 µl | 0 | 100 µl |
| Solution of peptide of formula (IV) | 400 µl | 400 µl | 400 µl | 400 µl |
| Liquid to be analyzed | 100 µl | 0 | 100 µl | 100 µl |
| 50 pg/ml standard endotoxin solution | 0 | 100 µl | 100 µl | 0 |

Solutions A, B, C, D are then treated according to either of the previously described operating procedures (a) and (b). The test with solution A enables any presence of proteases in the sample to be analyzed to be detected and to take account of this presence during the determination of endotoxins in the sample (test with solution D). The test with solution C, which contains an internal standard, makes it possible, by comparison with the tests related to solutions B and D, to detect any presence in the sample to be analyzed of products inhibiting the hydrolysis of the peptide of formula (IV) and to take account of this presence during the determination of endotoxins.

EXAMPLE 6 TO 8

Application of peptides of formula (I) in the determination of endotoxins

The procedure is as in Example 5 replacing initially the peptide of formula (IV) by one of the peptides of formulae (V), (VI), (VII). The excitation wavelength and the wavelength at which the fluoresecence intensity is measured, wavelength which is the emission wavelength of the free amine, are then as follows:

| Peptide used | Excitation wavelength | Wavelength at which the fluorescence intensity is measured |
|---|---|---|
| Formula (V) | 354 nm or 370 nm | 430 nm |
| Formula (VI) | 382 nm or 400 nm | 480 nm |
| Formula (VII) | 464 nm | 512 nm |

I claim:

1. Peptides of the formula:

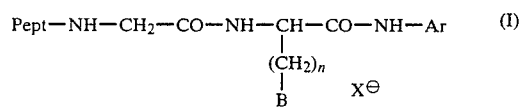

wherein Pept— is a hydrophobic peptide chain having 1 or 2 amino acid links, —NH—Ar is the residue of 7-amino 4-nitro 2-oxa 1,3-benzodiazole or 3-amino 9-ethyl carbazole n is equal to 1, 2, 3, 4 or 5 and B is a radical

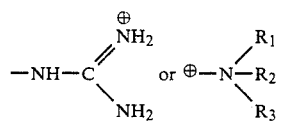

$R_1$, $R_2$ and $R_3$ designating hydrogen atoms or methyl groups.

2. Peptides according to claim 1 wherein n is equal to 3 and B is the group

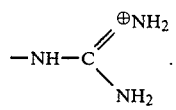

3. Peptides according to claim 1 wherein the hydrophobic peptide chain [Pept—] is chosen from the chains [Val—Leu—], [Ser (OBz)—], [Ile—Glu (γ-OCH₃)—], [Val—], [Leu—], [Val—Ser—], in which the amino group of the amino acid link, when there is only one link, and the amino group of the left-hand amino acid link, when there are two links, are not substituted or substituted by a tertiobutyloxycarbonyl, benzyloxycarbonyl, benzyl, tosyl or acyl group.
4. Peptide according to claim 3 having the formula:
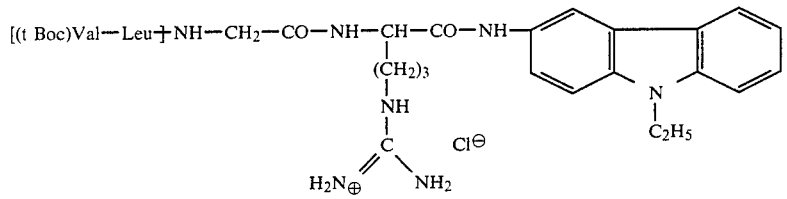
in which Leu is the leucine link and (t Boc) Val the valine link in which the amino group NH₂ is substituted by a tertiobutyloxycarbonyl group.
* * * * *